United States Patent
Lim et al.

(12) 
(10) Patent No.: US 11,464,988 B2
(45) Date of Patent: Oct. 11, 2022

(54) HEADER-LESS IMPLANTABLE MEDICAL DEVICE

(71) Applicant: Pacesetter, Inc., Sylmar, CA (US)

(72) Inventors: Wisit Lim, Santa Clarita, CA (US); Ofer Rosenzweig, West Hills, CA (US); Reza Shahandeh, Tarzana, CA (US); Alex Soriano, Ventura, CA (US)

(73) Assignee: PACESETTER, INC., Sylmar, CA (US)

( * ) Notice: Subject to any disclaimer, the term of this patent is extended or adjusted under 35 U.S.C. 154(b) by 81 days.

(21) Appl. No.: 16/920,021

(22) Filed: Jul. 2, 2020

(65) Prior Publication Data

US 2022/0001186 A1  Jan. 6, 2022

(51) Int. Cl.
*A61N 1/375* (2006.01)
*A61N 1/362* (2006.01)
*A61B 5/00* (2006.01)
*A61N 1/39* (2006.01)
*A61N 1/36* (2006.01)

(52) U.S. Cl.
CPC ............ *A61N 1/3752* (2013.01); *A61B 5/686* (2013.01); *A61N 1/362* (2013.01); *A61N 1/3605* (2013.01); *A61N 1/3956* (2013.01)

(58) Field of Classification Search
None
See application file for complete search history.

(56) References Cited

U.S. PATENT DOCUMENTS

| | | | | |
|---|---|---|---|---|
| 5,906,634 | A * | 5/1999 | Flynn | A61N 1/3752 607/37 |
| 6,498,951 | B1 * | 12/2002 | Larson | A61N 1/37512 607/36 |
| 10,084,278 | B2 | 9/2018 | Farr et al. | |
| 2010/0249869 | A1 * | 9/2010 | Ries | A61N 1/3752 607/37 |
| 2012/0185019 | A1 * | 7/2012 | Schramm | A61N 1/3752 607/72 |
| 2012/0253440 | A1 * | 10/2012 | Grohmann | A61N 1/3754 607/116 |
| 2012/0283806 | A1 * | 11/2012 | Troosters | A61N 1/3752 607/116 |
| 2013/0345770 | A1 | 12/2013 | Dianaty et al. | |
| 2019/0232066 | A1 * | 8/2019 | Lim | A61N 1/37512 |

* cited by examiner

*Primary Examiner* — Erica S Lee
(74) *Attorney, Agent, or Firm* — The Small Patent Law Group LLC; Dean D. Small

(57) ABSTRACT

A header-less implantable medical device, system and method are provided. The device includes an electronics module including circuitry, a battery, a receptacle assembly having an interior chamber and a receptable inlet configured to receive a lead connector assembly. A device housing has a case body that includes side walls and a peripheral edge that defines a single common chamber. The electronics module, battery and receptacle assembly are provided within the single common chamber. A connector opening is provided in the case body and joined to the receptacle inlet to form a passage through the case body into the interior chamber of the receptacle assembly.

21 Claims, 11 Drawing Sheets

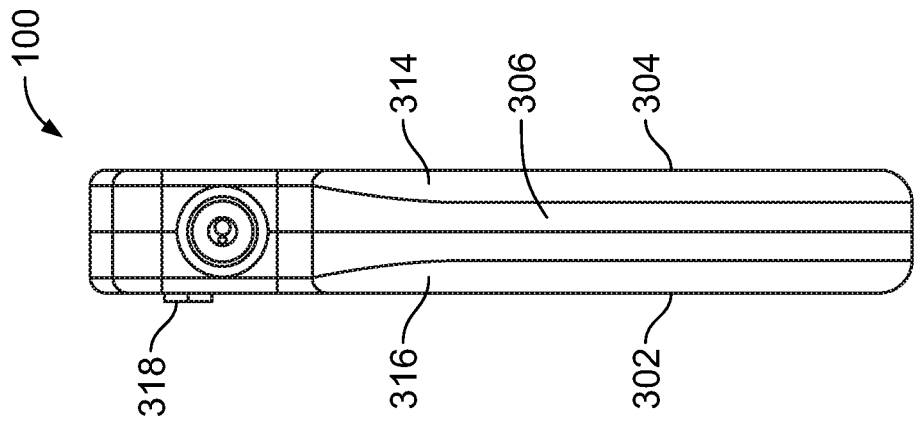
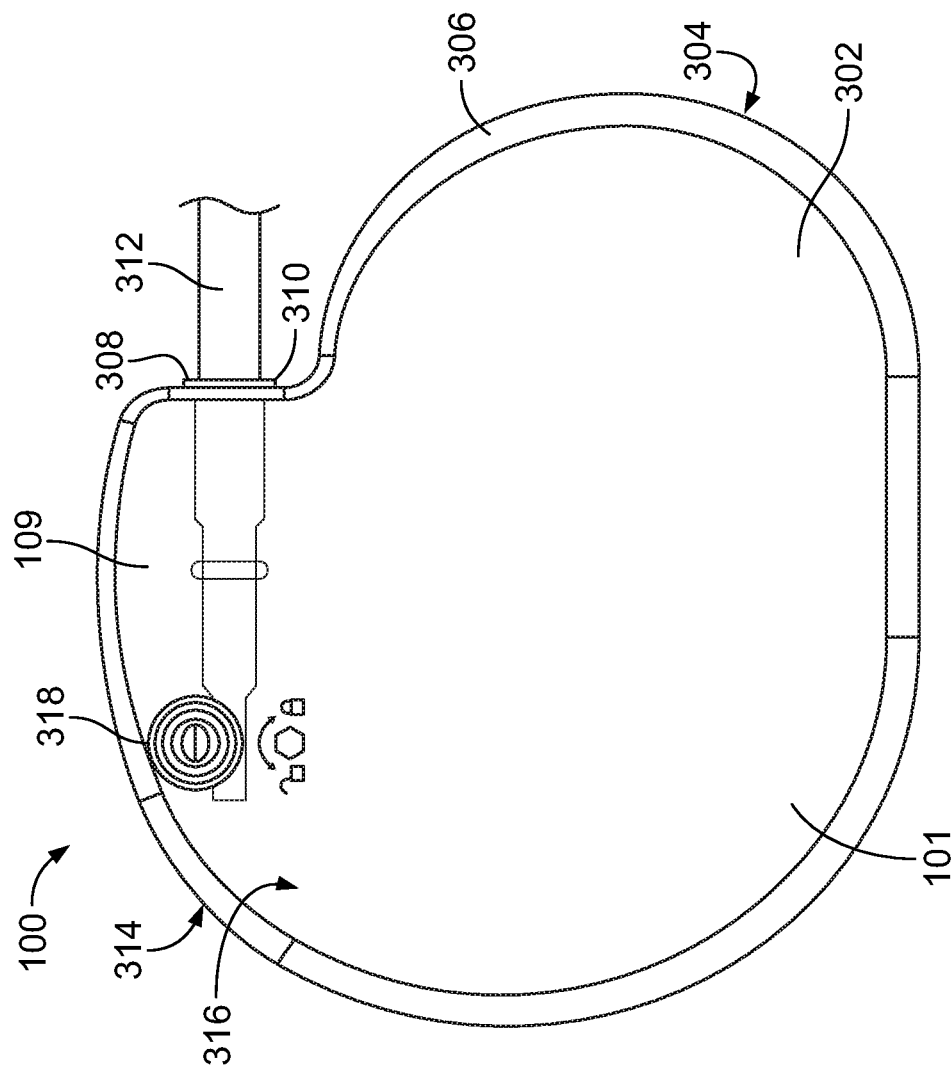

HEADER-LESS IMPLANTABLE MEDICAL DEVICE

BACKGROUND

Embodiments of the present disclosure generally relate to header-less implantable medical devices and associated methods.

Various types of implantable medical devices (IMDs), such as cardiac and neural stimulators, utilize circuitry within a housing or encasement to sense activity and/or generate therapeutic electrical stimulation pulses. The circuitry is electrically coupled to a header that is attached to the enclosure by a feedthrough assembly including a set of conductive pins. Implantable leads are configured to be inserted into a lead bore of the header and include electrical and mechanical connectors on a proximal end that engage the electrical and mechanical connectors within the lead bore of the header. The implantable leads also include electrodes near a distal end coupled to the electrical connectors at the proximal end via conductors, the electrodes configured to sense activity at and/or deliver a stimulus to tissue surrounding the electrodes.

Headers are commonly formed separately from and joined to the IMD housing (e.g., a titanium can). Headers may be formed by an epoxy cast in-place on an end of a case or housing of the IMD. Alternatively, headers may be pre-molded using a thermoplastic polyurethane composition, such as a Tecothane® composition, and then the pre-molded header is attached to the IMD housing. Prior to joining the header to the IMD housing, the feedthrough assembly needs to be attached to the IMD housing, e.g., by welding. Headers that are either cast in-place or pre-molded and attached to the IMD housing may provide a hermetic seal for the IMD housing. Additionally or alternatively, such headers may be optically transparent to facilitate visual confirmation of proper lead insertion into the header during implantation.

However, an opportunity remains to improve upon conventional IMD designs. The cost of and/or processes to attach the header and the feedthrough assembly to the IMD housing contribute to an increased overall price of the IMD, as well as potential failure modes of the IMD. For example, the header-IMD housing interface may be a source of lead abrasion. Additionally, difficulties exist in managing a reliable adhesion of the header to the IMD housing. Also, visual lead insertion confirmation is inherently subjective and may result in instances of improper confirmation.

Accordingly, a need remains for an implantable medical device that affords a reliable and simple integration of the header and the IMD housing and/or objective visual lead insertion confirmation.

SUMMARY

In accordance with embodiments herein, a header-less implantable medical device is provided. The device includes an electronics module including circuitry, a battery, a receptacle assembly having an interior chamber and a receptable inlet configured to receive a lead connector assembly. A device housing has a case body that includes side walls and a peripheral edge that defines a single common chamber. The electronics module, battery and receptacle assembly are provided within the single common chamber. A connector opening is provided in the case body and joined to the receptacle inlet to form a passage through the case body into the interior chamber of the receptacle assembly.

Optionally, the receptacle assembly may be held within the single common chamber of the case body in a header-less configuration. The electronics module may further comprise a flexible circuit having conductors with first and second ends. The first end may be connected to the circuitry and the second end may be connected to the receptacle assembly in a feedthrough-less configuration. The case body may be generally planar opposed side walls and a peripheral edge that may have an envelope that is generally oval shaped. The peripheral edge may have a notch formed therein to provide a flat surface at the connector opening.

Optionally, the case body may include first and second shells that are hermetically sealed with one another to form the single common chamber. The first and second shells may include upper and lower sections. The upper section may enclose the receptacle assembly. The lower section may enclose the electronics module and battery. The upper and lower sections of each of the first and second shells may be formed from monolithic homogeneous material.

Optionally, the interior chamber may include sealing flanges wrapping about an interior of the interior chamber. The sealing flanges may be formed of a non-conductive material. The sealing flanges may be configured to flex and frictionally receive the lead connector assembly to prevent bodily fluid from migrating along the lead connector assembly into the interior chamber. The receptacle assembly may include a contact element sandwiched between first and second non-conductive support elements that wrap about the interior chamber. The contact element may be bonded to the first and second non-conductive elements to form a hermetic seal thereby. The hermetic seal may separate the interior chamber from the single common chamber within the case body.

Optionally, the contact element may include a contact spring and a contact ring arranged concentric with one another. The contact spring may extend about and may protrude into the interior chamber. The contact ring may extend circumferentially about the contact spring and may be electrically connected to the electronics module. The device may include a lead engagement sensing circuit that may be configured to detect when the lead connector assembly is engaged with the receptacle assembly. The device may include a lead having a proximal end that may include the lead connector assembly and a distal end with one or more electrodes. The lead may be configured to at least one of: i) sense activity or ii) deliver a stimulus to tissue surrounding the one or more electrodes.

In accordance with embodiments herein, an implantable system is provided. The system includes an electronics module including circuitry, a battery, a receptacle assembly having an interior chamber and a receptable inlet configured to receive a lead connector assembly. A device housing has a case body that includes side walls and a peripheral edge that defines a single common chamber. The electronics module, battery and receptacle assembly are provided within the single common chamber. A connector opening is provided in the case body and joined to the receptacle inlet to form a passage through the case body into the interior chamber of the receptacle assembly. A lead has a proximal end that includes the lead connector assembly and a distal end with one or more electrodes. The lead is configured to at least one of: i) sense activity or ii) deliver a stimulus to tissue surrounding the one or more electrodes.

Optionally, the receptacle assembly may be held within the single common chamber of the case body in a header-less configuration. The receptacle assembly may include a lead engagement assembly. The lead engagement assembly may include a set screw advanceable within a threaded bore configured to retain a proximal end of the lead connector assembly. One or more of the case body or the lead engagement assembly may include an integrated septum. The septum may be configured to allow access to a head of the set screw while inhibiting ingress of fluids into the lead engagement assembly.

Optionally, the interior chamber may include sealing flanges wrapping about an interior of the interior chamber. The sealing flanges may be formed of a non-conductive material. The sealing flanges may be configured to flex and frictionally receive the lead connector assembly to prevent bodily fluid from migrating along the lead connector assembly into the interior chamber. The receptacle assembly may include a contact element sandwiched between first and second non-conductive support elements that wrap about the interior chamber. The contact element may be bonded to the first and second non-conductive elements may form a hermetic seal thereby. The hermetic seal may separate the interior chamber from the single common chamber within the case body.

In accordance with embodiments herein, a method to provide header-less implantable medical device is provided. The method provides first and second shells of a case body of a device housing. The case body includes a connector opening provided in one or more of the first and second shells. The method mounts an electronics module including circuitry, a battery, and a receptacle assembly within the first and second shells. The receptacle assembly has an interior chamber and a receptable inlet configured to receive a lead connector assembly. The mounting includes locating the receptacle inlet at the connector opening. The method joins the first and second shells to form the case body. The case body includes side walls and a peripheral edge that define a single common chamber. The electronics module, battery and receptacle assembly are provided within the single common chamber. The joining includes joining the receptacle inlet to the connector opening to form a passage through the case body into the interior chamber of the receptacle assembly.

Optionally, the receptacle assembly may be held within the single common chamber of the case body in a header-less configuration. The electronics module may further comprise a flexible circuit having conductors with first and second ends. The method may further comprise connecting a first end of the conductors to the circuitry and connecting the second end to the receptacle assembly in a feedthrough-less configuration. The joining may include hermetically sealing the first and second shells with one another.

Optionally, the method may comprise forming the receptacle assembly. The forming the receptacle assembly may include sandwiching a contact element between first and second non-conductive support elements and bonding the contact element to the first and second non-conductive support elements to form a hermetic seal therebetween. Each of the contact element and the first and second non-conductive support elements may wrap about the interior chamber, and the hermetic seal may separate the interior chamber from the single common chamber within the case body. The method may comprise forming the contact element. The forming the contact element may include arranging a contact ring concentric with a contact spring such that the contact spring extends about and protrudes into the interior chamber and the contact ring extends circumferentially about the contact spring to provide a direct electrical connection to the interior chamber for the circuitry of the electronics module.

BRIEF DESCRIPTION OF THE DRAWINGS

FIG. 3 illustrates a side perspective view of the IMD of FIG. 1 in accordance with embodiments herein.

FIG. 4 illustrates an end perspective view of the IMD of FIG. 1 in accordance with embodiments herein.

DETAILED DESCRIPTION

Figure 1:
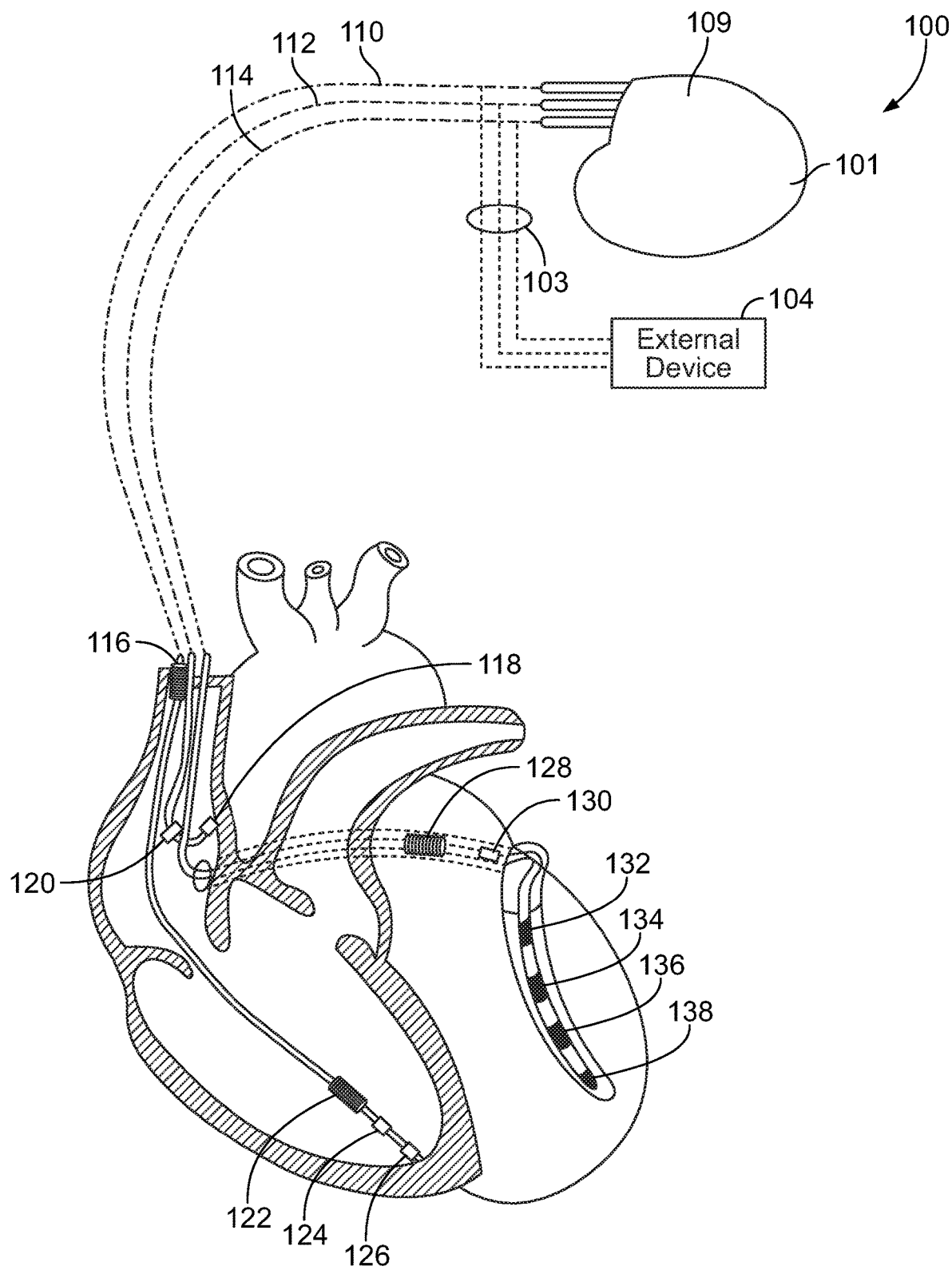
FIG. 1 illustrates an IMD and external device coupled to a heart in a patient and implemented in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "header-less" shall mean an implantable medical device that does not include a header. For example, a header-less IMD does not include a header formed by an epoxy cast in-place on an IMD housing and/or a pre-molded header attached to the IMD housing.

The term "feedthrough-less" shall mean an implantable medical device that does not include a feedthrough assembly. For example, a feedthrough-less IMD does not include an assembly of conductive pins or other conductive interconnects that electrically couple a header to circuitry and/or a battery within a housing of an IMD. In some examples, a feedthrough assembly is joined to an IMD housing intermediate to joining a header to the IMD housing.

The term "single common chamber" shall mean a single physical space that does not include any intermediate barriers hermetically separating one section from another within the physical space. For the avoidance of doubt, air and other flowable medium shall be permitted to move throughout an entirety of the single common chamber.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

System Overview

Embodiments herein include systems, devices, and methods of providing header-less IMDs. Such systems, devices, and methods integrate a receptacle assembly into a single common chamber of the case body of the IMD, along with the IMD circuitry and the battery, in a header-less configuration. Additionally or alternatively, embodiments herein provide for feedthrough-less and/or direct electrical connection between a hermetic interior chamber of the receptacle assembly and the IMD circuitry within the single common chamber of the case body. Accordingly, embodiments herein provide for an IMD that integrates the functionality of a conventional header into the IMD housing and eliminates the need for an intermediate feedthrough assembly to establish electrical connection between a header joined to or formed on the IMD housing and IMD circuitry within a hermetic IMD housing. Eliminating a header that is joined to or formed on the IMD housing eliminates use of epoxy backfill and corresponding failure modes resulting from adhesive delamination. Integrating the receptacle assembly, IMD circuitry, and battery into the single common chamber of the case body may also provide for an IMD housing that is smooth and lacks transitions between separate components that may cause lead-to-can abrasion.

Further additionally or alternatively, embodiments herein provide for a lead engagement detection circuit for objectively confirming lead insertion and engagement within the receptacle assembly. The lead engagement detection circuit provides an objective means for confirming proper lead engagement within the receptacle assembly, eliminating the need for visual confirmation of lead engagement.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference in their entireties.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference in their entireties. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference in their entireties.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may be a leadless cardiac monitor (ICM) that includes one or more structural and/or functional aspects of the device(s) described in U.S. patent application Ser. No. 15/084,373, filed Mar. 29, 2016, entitled, "Method And System To Discriminate Rhythm Patterns In Cardiac Activity," which is hereby incorporated by reference in its entirety. Additionally or alternatively, the IMD may be an ICM that includes one or more structural and/or functional aspects of the device(s) and/or method(s) described in U.S. patent application Ser. No. 15/973,126, titled "Method And System For Second Pass Confirmation Of Detected Cardiac Arrhythmic Patterns"; U.S. patent application Ser. No. 15/973,351, titled "Method And System To Detect R-Waves In Cardiac Arrhythmic Patterns"; U.S. patent application Ser. No. 15/973,307, titled "Method And System To Detect Post Ventricular Contractions In Cardiac Arrhythmic Patterns"; and U.S. patent application Ser. No. 16/399,813, titled "Method And System To Detect Noise In Cardiac Arrhythmic Patterns".

Embodiments may be implemented in connection with one or more PIMDs. Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the PIMD may include one or more structural and/or functional aspects of the device(s) described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

All references, including publications, patent applications and patents, cited herein are hereby incorporated by reference to the same extent as if each reference were individually and specifically indicated to be incorporated by reference and were set forth in its entirety herein.

FIG. 1 illustrates an IMD 100 and external device 104 coupled to a heart in a patient and implemented in accordance with embodiments herein. The external device 104 may be a programmer, an external defibrillator, a workstation, a portable computer, a personal digital assistant, a cell phone, a bedside monitor, or the like. The IMD 100 may represent a cardiac monitoring device, pacemaker, cardioverter, cardiac rhythm management device, defibrillator, neurostimulator, leadless monitoring device, leadless pacemaker or the like, implemented in accordance with one embodiment of the present invention. The IMD 100 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the IMD 100 are discussed and illustrated in the drawings herewith.

The IMD 100 includes a device housing 101 that includes an upper section 109 including a receptacle assembly configured to receive a lead connector assembly for one or more of a right ventricular lead 110, a right atrial lead 112, and a coronary sinus lead 114, or the like. The leads 112, 114 and 110 measure cardiac signals of the heart. The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

During implantation, the external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Optionally, the external device 104 may not be directly connected to the leads 112, 114 and 110. Instead, the IEGM cardiac signals sensed by the leads 112, 114 and 110 may be collected by the IMD 100 and transmitted wirelessly to the external device 104. Hence, the external device 104 receives the IEGM cardiac signals through telemetry circuit inputs. The physician or another user controls operation of the external device 104 through a user interface.

Implantable Medical Device

Figure 2:
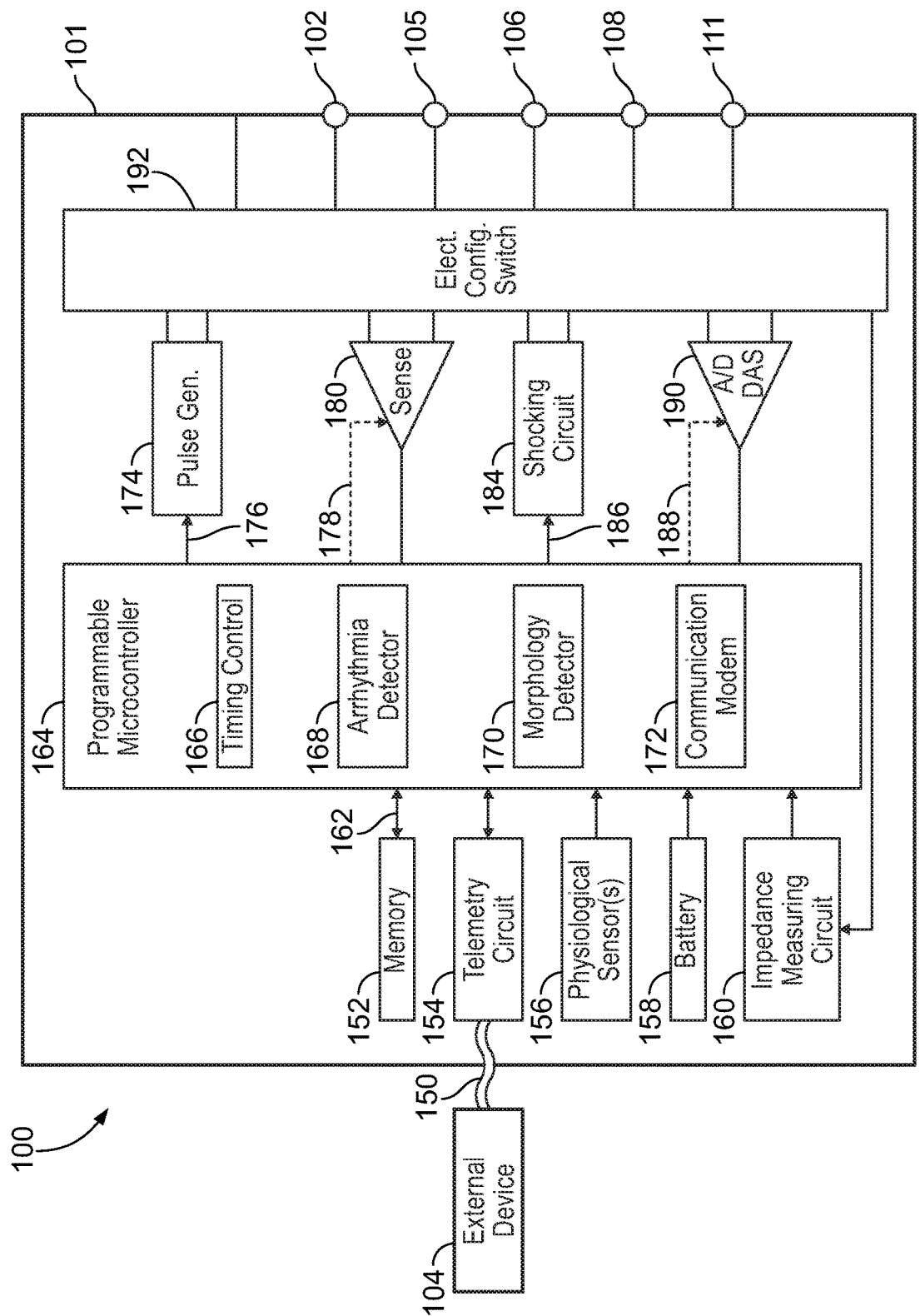
FIG. 2 illustrates a block diagram of the IMD of FIG. 1 in accordance with embodiments herein.

FIG. 2 illustrates a block diagram of the IMD 100 of FIG. 1 in accordance with embodiments herein. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing.

The IMD 100 has a device housing 101 to hold the electronic/computing components. The device housing 101 (which is often referred to as the "can", "case", "encasing", or "case electrode") may be programmably selected to act as the return electrode for certain stimulus modes. The device housing 101 further includes a connector (not shown) with a plurality of terminals 102, 105, 106, 108, and 111. The terminals may be connected to electrodes that are located in various locations within and about the heart. For example, the terminals may include: a terminal 102 to be coupled to an first electrode (e.g., a tip electrode) located in a first chamber; a terminal 105 to be coupled to a second electrode (e.g., tip electrode) located in a second chamber; a terminal 106 to be coupled to an electrode (e.g., ring) located in the first chamber; a terminal 108 to be coupled to an electrode located (e.g., ring electrode) in the second chamber; and a terminal 111 to be coupled to an electrode (e.g., coil) located in the SVC. The type and location of each electrode may vary. For example, the electrodes may include various combinations of ring, tip, coil and shocking electrodes and the like.

The IMD 100 includes a programmable microcontroller 164 that controls various operations of the IMD 100, including cardiac monitoring and stimulation therapy. Microcontroller 164 includes one or more microprocessors or CPUs (or equivalent control circuitry), RAM and/or ROM memory, logic and timing circuitry, state machine circuitry, and I/O circuitry.

The IMD 100 further includes a first chamber pulse generator 174 that generates stimulation pulses for delivery by one or more electrodes coupled thereto. The pulse generator 174 may deliver pacing pulses and/or anti-tachy pacing therapy. The pulse generator 174 is controlled by the microcontroller 164 via control signal 176. The pulse generator 174 is coupled to the select electrode(s) via an electrode configuration switch 192, which includes multiple switches for connecting the desired electrodes to the appropriate I/O circuits, thereby facilitating electrode programmability. The switch 192 is controlled by a control signal 186 from the microcontroller 164. In the example of FIG. 2, a single pulse generator 174 is illustrated. Optionally, the IMD 100 may include multiple pulse generators, similar to pulse generator 174, where each pulse generator is coupled to one or more electrodes and controlled by the microcontroller 164 to deliver select stimulus pulse(s) to the corresponding one or more electrodes.

The microcontroller 164 is illustrated to include timing control circuitry 166 to control the timing of the stimulation pulses (e.g., pacing rate, atrio-ventricular (AV) delay, atrial interconduction (A-A) delay, or ventricular interconduction (V-V) delay, etc.). The timing control circuitry 166 may also be used for the timing of refractory periods, blanking intervals, noise detection windows, evoked response windows, alert intervals, marker channel timing, and so on. Microcontroller 164 also has an arrhythmia detector 168 for detecting arrhythmia conditions, and a morphology detector 170 to review and analyze one or more features of the morphology of cardiac signals. Although not shown, the microcontroller 164 may further include other dedicated circuitry and/or firmware/software components that assist in monitoring various conditions of the patient's heart and managing pacing therapies.

The IMD 100 is equipped with a communication modem (modulator/demodulator) 172 to enable wireless communication with other devices, implanted devices and/or external devices. In one implementation, the communication modem 172 may use high frequency modulation of a signal transmitted between a pair of electrodes. In one implementation, the communication modem 172 uses high frequency modulation, for example using RF, Bluetooth, or Bluetooth Low Energy telemetry protocols. The signals are transmitted in a high frequency range and will travel through the body tissue in fluids without stimulating the heart or being felt by the patient. The communication modem 172 may be implemented in hardware as part of the microcontroller 164, or as software/firmware instructions programmed into and executed by the microcontroller 164. Alternatively, the communication modem 172 may reside separately from the microcontroller as a standalone component. The communication modem 172 facilitates data retrieval from a remote monitoring network. The communication modem 172 enables timely and accurate data transfer directly from the patient to an electronic device utilized by a physician.

The IMD 100 includes sensing circuitry 180 selectively coupled to one or more electrodes that is configured to obtain biological signals (e.g., cardiac activity signals, neurological activity signals, and the like) indicative of biological behavior of an anatomy of interest over a period of time. For example, the sensing circuitry 180 performs sensing operations through the switch 192 to detect the presence of cardiac activity in the right chambers of the heart. The sensing circuitry 180 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuits, similar to sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or in a bipolar sensing configuration.

The IMD 100 further includes an analog-to-digital (A/D) data acquisition system (DAS) 190 coupled to one or more electrodes via the switch 192 to sample cardiac signals across any pair of desired electrodes. The data acquisition system 190 is configured to acquire intracardiac electrogram signals, convert the raw analog data into digital data, and store the digital data for later processing and/or telemetric transmission to an external device 104 (e.g., a programmer, local transceiver, or a diagnostic system analyzer). The data acquisition system 190 is controlled by a control signal 188 from the microcontroller 164.

The microcontroller 164 is coupled to a memory 152 by a suitable data/address bus 162. The programmable operating parameters used by the microcontroller 164 are stored in memory 152 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 100 may be non-invasively programmed into the memory 152 through a telemetry circuit 154 in telemetric communication via communication link 150 with the external device 104. The telemetry circuit 154 allows intracardiac electrograms and status information relating to the operation of the IMD 100 (as contained in the microcontroller 164 or memory 152) to be sent to the external device 104 through the established communication link 150.

The IMD 100 may further include magnet detection circuitry (not shown), coupled to the microcontroller 164, to detect when a magnet is placed over the unit. A magnet may be used by a clinician to perform various test functions of the unit 100 and/or to signal the microcontroller 164 that the external programmer is in place to receive or transmit data to the microcontroller 164 through the telemetry circuits 154.

The IMD 100 may further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. The microcontroller 164 responds by adjusting the various pacing parameters (such as rate, AV Delay, V-V Delay, etc.) at which the atrial and ventricular pacing pulses are administered. While shown as being included within the unit 100, the physiologic sensor(s) 156 may be external to the unit 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 158 provides operating power to all of the components in the IMD 100. The battery 158 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the unit 100 employs lithium/silver vanadium oxide batteries.

Optionally, the IMD 100 further includes an impedance measuring circuit 160, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used. Optionally, the microcontroller 164 further controls a shocking circuit 184 by way of a control signal 186. The shocking circuit 184 generates shocking pulses of low (e.g., up to 0.5 joules), moderate (e.g., 0.5-10 joules), or high energy (e.g., 111 to 40 joules), as controlled by the microcontroller 164.

The IMD 100 may be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 164 further controls a shocking circuit 184 by way of a control signal 186. The shocking circuit 180 generates shocking pulses of low (e.g., up to 0.5 joules), moderate (e.g., 0.5-10 joules), or high energy (e.g., 11 to 40 joules), as controlled by the microcontroller 164. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD 100.

It is recognized that the configurations of circuitry and microcontrollers illustrated herein are by way of example only. Optionally, operations described in connection with the microcontroller may be implemented by circuitry (e.g., firmware and/or discrete circuitry). Optionally, operations described in connection with the circuitry (e.g., firmware and/or discrete circuitry) may be implemented by the microcontroller.

FIGS. 3 and 4 illustrate side and end perspective views of the IMD of FIG. 1 in accordance with embodiments herein. The IMD 100 includes a device housing 101. The device housing 101 includes a case body having side walls 302, 304 and a peripheral edge 306 that define a single common chamber. The single common chamber may be configured to hold at least an electronics module, a battery, and a receptacle assembly, as described further below. The opposed side walls 302, 304 of the case body may be generally planar. The peripheral edge 306 of the case body may have an envelope that is generally oval shaped. A connector opening 308 may be provided in the case body. The peripheral edge 306 may have a notch 310 formed in the envelope to provide a flat surface at the connector opening 308. The connector opening 308 is joined to a receptacle inlet of the receptacle assembly disposed in an upper section 109 of the device housing 101 to form a passage through the case body into an interior chamber of the receptacle assembly 109 to receive a lead (e.g., a right ventricular lead 110, a right atrial lead 112, a coronary sinus lead 114, etc.). The lead may be configured to sense activity and/or deliver a stimulus to tissue surrounding the one or more electrodes. The lead may have a proximal end that includes a lead connector assembly 312 and a distal end with one or more electrodes (e.g., an atrial tip electrode 118, an atrial ring electrode 120, a left atrial ring electrode 128, a left atrial coil electrode 130, one or more left ventricular electrodes 132-138, etc.). The case body may include first and second shells 314, 316 that are hermetically sealed with one another to form the single common chamber. A septum 318 may also be provided in the case body, the septum 318 for preventing fluid or tissue ingress into the housing 101, such as during implantation (e.g., during adjustment of an underlying lead engagement assembly of the receptacle assembly). Additionally or alternatively, the device housing 101 may include one or more suture holes (not shown) provided thereon to facilitate implantation of the IMD 100.

Figure 5:
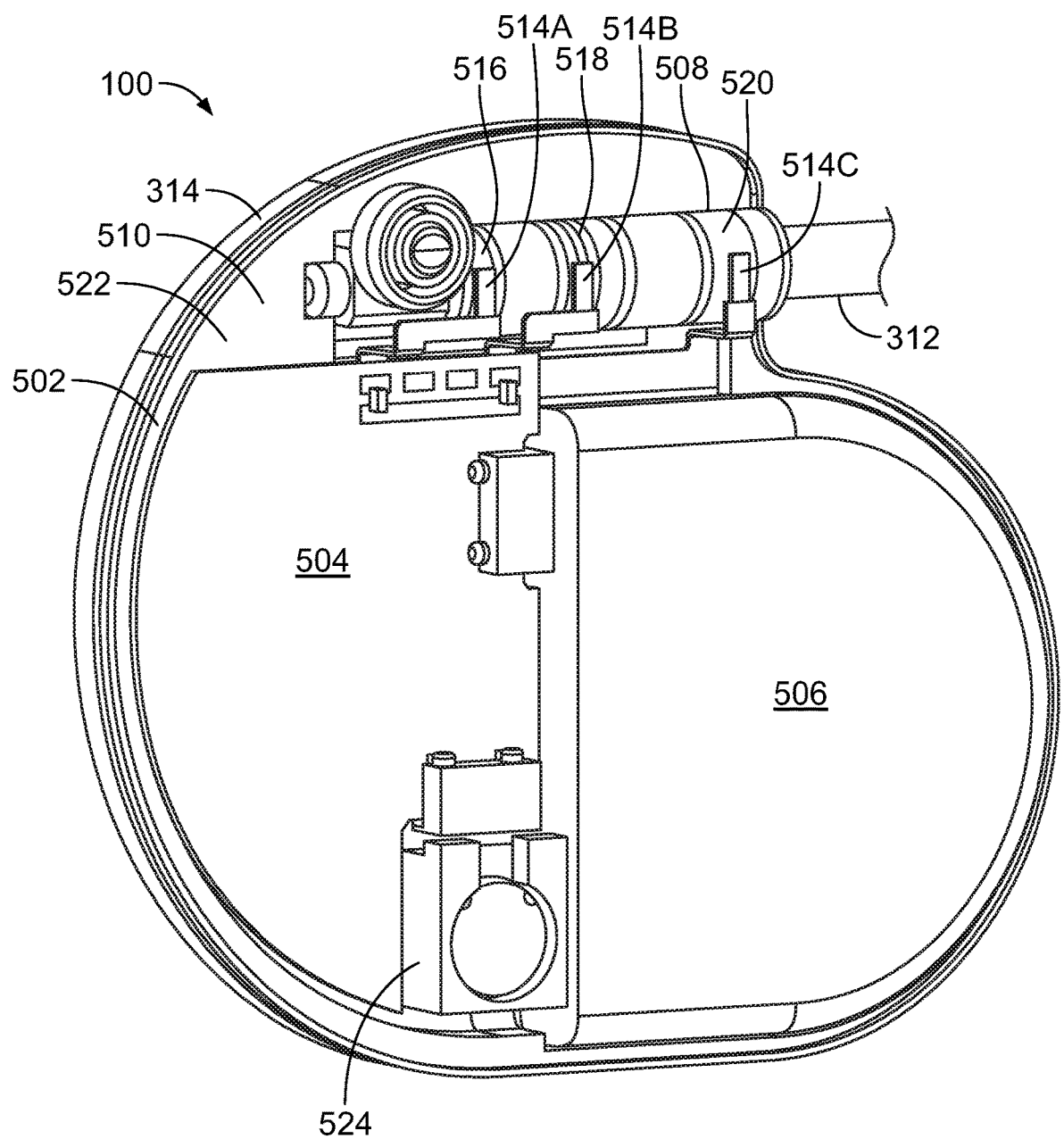
FIG. 5 illustrates a side perspective view of the IMD of FIG. 1 with a portion of the case body removed in accordance with embodiments herein.

FIG. 5 illustrates a side perspective view of the IMD of FIG. 1 with a portion of the case body removed in accordance with embodiments herein. An electronics module 504, a battery 506, and a receptacle assembly 508 are provided in the single common chamber 502 defined by the side walls 302, 304 and the peripheral edge 306 of the case body. The single common chamber 502 is a single physical space that does not include any intermediate barriers hermetically separating one section of the physical space occupied by the electronics module 504 and/or the battery 506 from another physical space occupied by the receptacle assembly 508. For example, the first and second shells 314, 316 may include upper sections 510 and lower sections 512 that are not hermetically separated upon hermetically sealing the first and second shells 314, 316. The upper sections 510 may enclose the receptacle assembly 508. The lower sections 512 may enclose the electronics module 504 and the battery 506. Additionally or alternatively, the upper and lower sections 510, 512 of each of the first and second shells 314, 316 may be formed from monolithic homogeneous material. Further additionally or alternatively, a frame 522 (e.g., a plastic frame) may be provided to facilitate assembly of one or more of the electronics module 504, the battery 506, and the receptacle assembly 508 within the single common chamber 502. The IMD 100 may also include an inductive circuit 524 and/or a telemetry circuit 154 (shown in FIG. 2) configured for telemetric communication with an external device 104.

The receptacle assembly 508 is held within the single common chamber 502 of the case body in a header-less configuration. For example, the receptacle assembly 508 is included in the single common chamber 502 itself and is neither cast in-place on nor pre-molded and attached to the device housing 101. Additionally or alternatively, the receptacle assembly 508 is connected to the electronics module 504 in a feedthrough-less configuration. For example, the electronics module 504 includes conductors that directly contact the receptacle assembly 508 and no assembly of conductive pins/interconnects is provided intermediate the electronics module 504 and the receptacle assembly 508. The electronics module 504 may include conductors 514A, 514B, 514C with first and second ends. The first ends of the conductors 514A, 514B, 514C may be connected to the IMD circuitry. The second ends of the conductors 514A, 514B, 514C may be directly connected to the receptacle assembly 508. For example, the conductors 514A, 514B, 514C may be connected, respectively, to a tip electrode 516, a ring electrode 518, and a case electrode 520 of the receptacle assembly 508.

Figure 6:
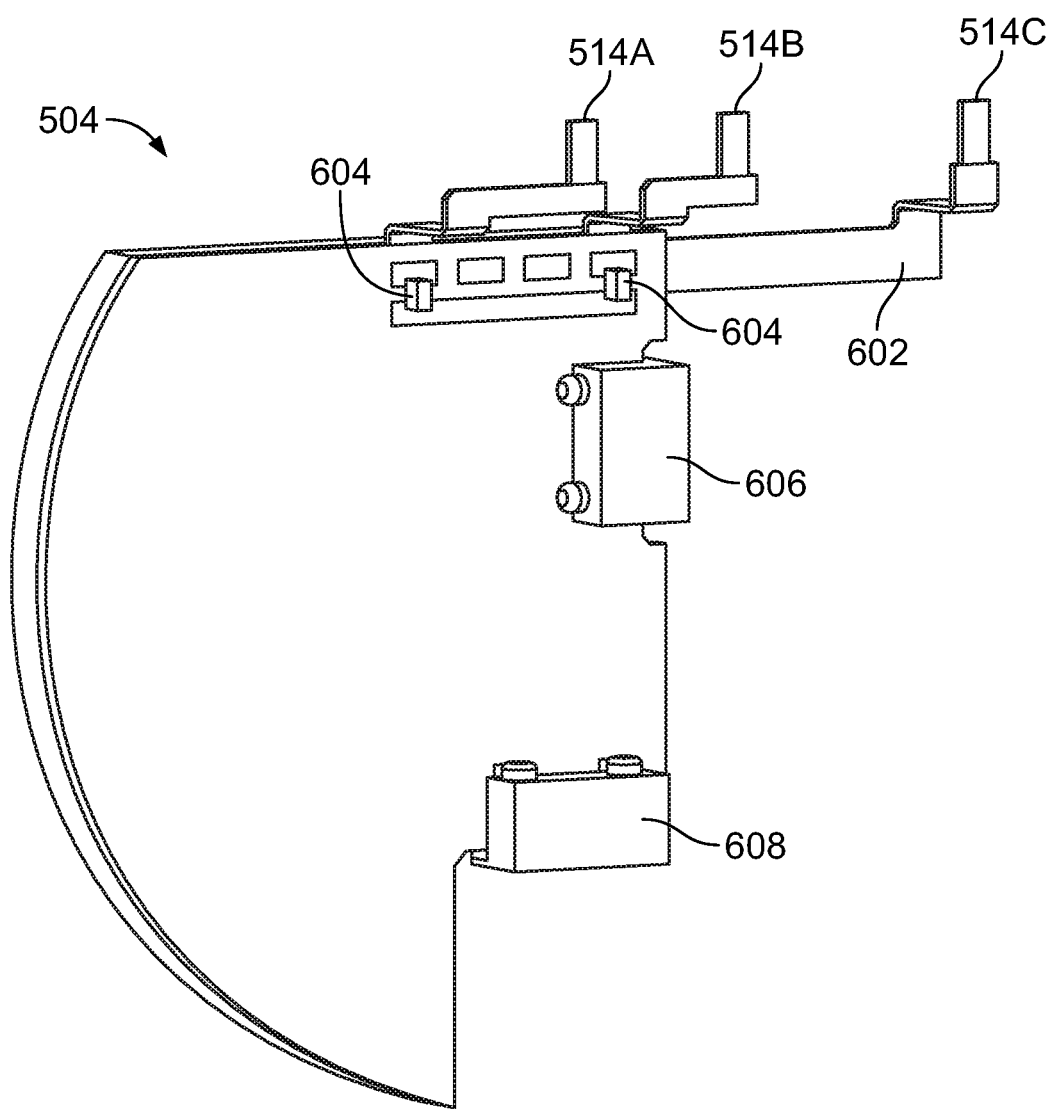
FIG. 6 illustrates a side perspective view an electronics module in accordance with embodiments herein.

FIG. 6 illustrates a side perspective view of an electronics module 504 in accordance with embodiments herein. The electronics module 504 may include a flexible circuit 602. The flexible circuit 602 may include the conductors 514A, 514B, 514C. The conductors 514A, 514B, 514C may be connected to the IMD circuitry (e.g., the microcontroller 164, the pulse generator 174, the sensing circuitry 180, the A/D DAS 190, EMI filters 604, etc.) at the first end. The second ends of the conductors 514A, 514B, 514C may be electrically connected to the receptacle assembly 508 using a non-hermetic connection (e.g., flex bonding, wire bonding, or the like). When the lead connector assembly 312 of a lead is engaged in the receptacle assembly 508, direct electrical communication between the IMD circuitry and the lead may be established. The electronics module 504 may also include a battery connector 606. Additionally or alternatively, the electronics module 504 may include an inductor circuit connector 608 and/or a telemetry circuit connector (not shown).

Figure 7:
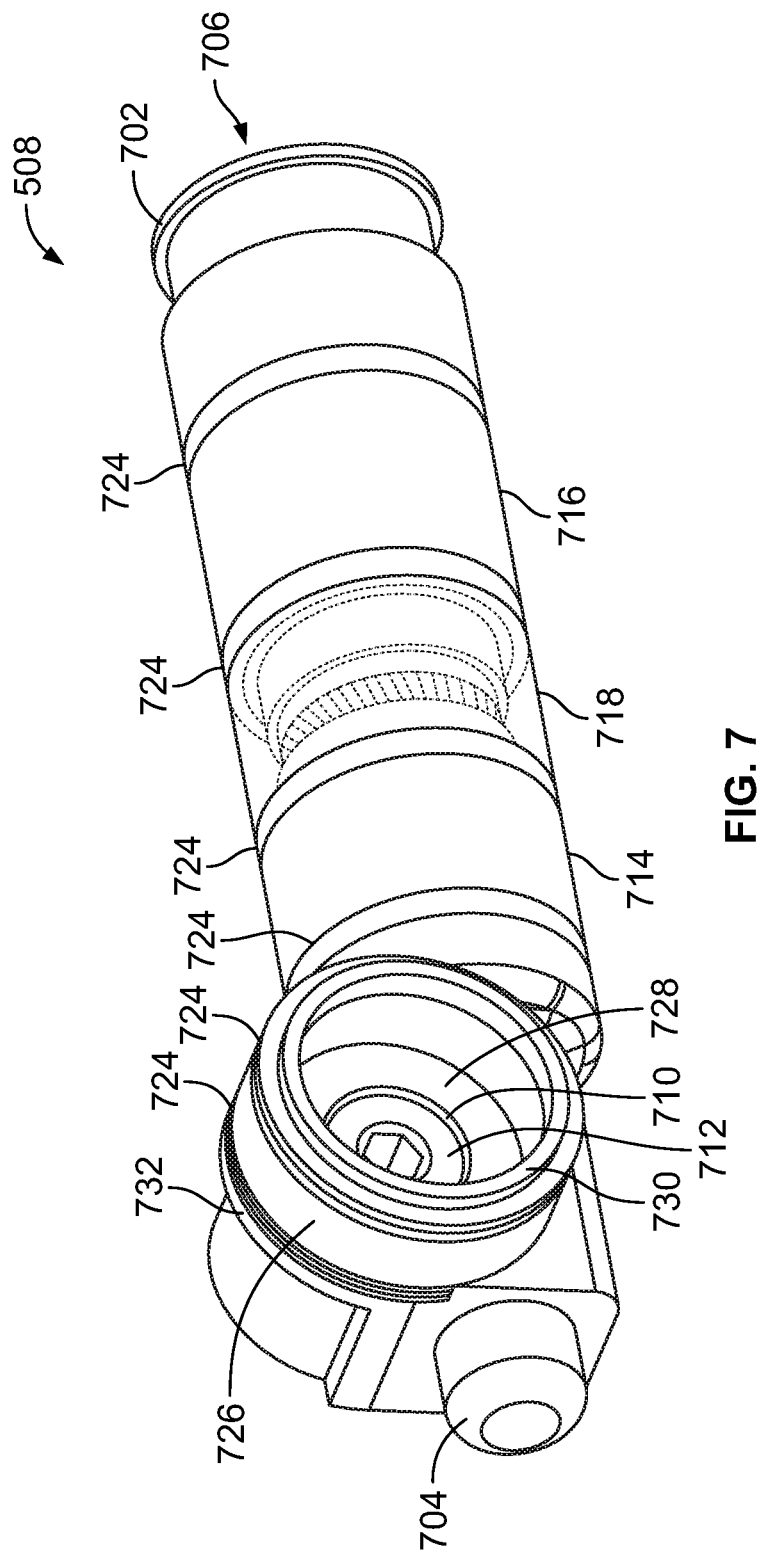
FIG. 7 illustrates a side perspective view of a receptacle assembly in accordance with embodiments herein.

FIG. 7 illustrates a side perspective view of a receptacle assembly 508 in accordance with embodiments herein. The receptacle assembly 508 extends between a distal receptacle inlet 702 and a proximal tip 704. An interior chamber 706 disposed in the receptacle assembly 508 may extend from the receptacle inlet 702 to a lead engagement assembly 710. The lead engagement assembly 710 may be positioned at or distal to the tip 704. The lead engagement assembly 710 includes a set screw 712 movably engaged within a set screw bore. The set screw 712 may be configured to engage a proximal end of the lead connector assembly 312 upon advancement within the set screw bore and vice-versa. The set screw 712 (accessed through the septum 318) may be advanced within the set screw bore towards the proximal end of the lead connector assembly 312 to secure the lead connector assembly 312 within the receptacle assembly 508.

The receptacle assembly 508 includes a contact element 718 sandwiched between first and second non-conductive support elements 714, 716 that wrap about the interior chamber 706. The contact element 718 may be bonded to the first and second non-conductive elements 714, 716 to form a hermetic seal. For example, the first and second non-conductive support elements 714, 716 may be formed from a ceramic material. A conductive intermediate material 724 (e.g., gold) may be sputtered onto portions of the first and second non-conductive support elements 714, 716. The contact element 718 may be joined (e.g., by brazing or the like) to the first and second non-conductive elements 714, 716 via the intermediate material 724. The receptacle inlet 702 may be similarly hermetically bonded to a distal end of the second non-conductive support element 716 via the intermediate material 724. Additionally or alternatively, a proximal end of the receptacle assembly 508 (e.g., including the lead engagement assembly 710 and/or the tip 704) may be similarly hermetically bonded to a proximal end of the first non-conductive support element 714 via the intermediate material 724. Additionally or alternatively, a third non-conductive support element 726 that wraps around a septum bore 728 may be similarly hermetically bonded to a septum opening 730 and a lead engagement assembly ring 732 of the lead engagement assembly 710. Further additionally or alternatively, metal components may be hermetically bonded to other metal components by, for example and without limitation, welding, brazing, or the like. The hermetic seals separate the interior chamber 706 from the single common chamber 502 within the case body.

Figure 8:
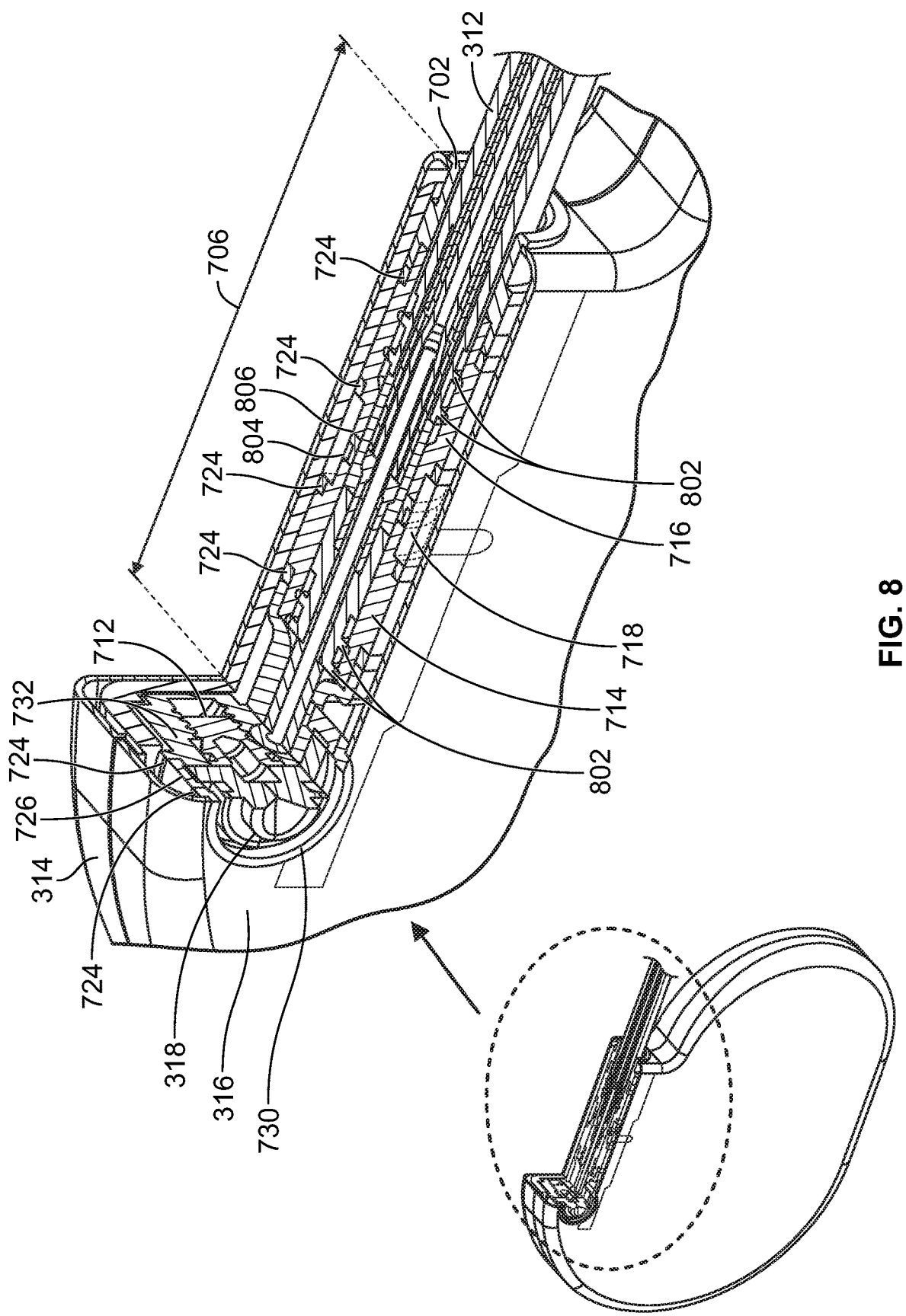
FIG. 8 illustrates a side perspective view of the IMD of FIG. 1 with a portion of the receptacle assembly and case body removed in accordance with embodiments herein.

FIG. 8 illustrates a side perspective view of the IMD of FIG. 1 with a portion of the receptacle assembly 508 and case body removed in accordance with embodiments herein. The interior chamber 706 of the receptacle assembly 508 may extend from the receptacle inlet 702 to the lead engagement assembly 710. A lead connector assembly 312 is shown engaged in the interior chamber 706 of the receptacle assembly 508. The interior chamber 706 may include sealing flanges 802 wrapping about an interior of the interior chamber. The sealing flanges 802 may be formed of a non-conductive material (e.g., silicone or the like). Additionally or alternatively, the sealing flanges 802 may be configured to flex and frictionally receive the lead connector assembly 312 to prevent bodily fluid from migrating along the lead connector assembly 312 into the interior chamber 706. The contact element 718 of the receptacle assembly is hermetically bonded to the first and second non-conductive support elements 714, 716 via the sputtered conductive intermediate material 724 to form hermetic seals separating the interior chamber 706 and the single common chamber 502 within the case body. The contact element 718 may include a contact spring 804 and a contact ring 806 arranged concentric with one another. The contact spring 804 may extend about and protrude into the interior chamber 706. For example, the contact spring 804 may be a garter spring. The contact ring 806 may extend circumferentially about the contact spring 804 and electrically connect to the electronics module 504.

The receptacle assembly 508 may also include the receptacle inlet 702. The receptacle inlet 702 may be hermetically bonded to the distal end of the second non-conductive support element 716 via the intermediate material 724. Additionally or alternatively, the receptacle assembly 508 may also include a proximal end (e.g., including the lead engagement assembly 710 and/or the tip 704). All or a portion of the proximal end may be similarly hermetically bonded to a proximal end of the first non-conductive support element 714 via the intermediate material 724.

The receptacle assembly 508 may also include a lead engagement assembly 710 at or distal to the tip 704. The lead engagement assembly 710 may include a third non-conductive support element 726 that wraps around a septum bore 728. The third non-conductive support element 726 may be hermetically bonded via the sputtered intermediate material 724 to the septum opening 730 and a lead engagement assembly ring 732. Additionally or alternatively, the lead engagement assembly 710 may include a set screw 712 positioned within a threaded set screw bore 808. The set screw 712 may be configured to engage and retain the proximal end of the lead connector assembly 312 upon advancement within the set screw bore 808 and vice-versa. Additionally or alternatively, advancement of the set screw 712 within the set screw bore 808 of the lead engagement assembly may establish an electrical connection with the lead. A head of the set screw 712 may be accessed through the septum 318. The septum 318 may be a split septum configured to prevent the ingress of fluid and/or tissue into the lead engagement assembly 710. The septum 318 may be integrated into the case body and/or the lead engagement assembly 710. Accordingly, the septum 318 requires no adhesive to secure the septum to the IMD housing 101.

Figure 9:
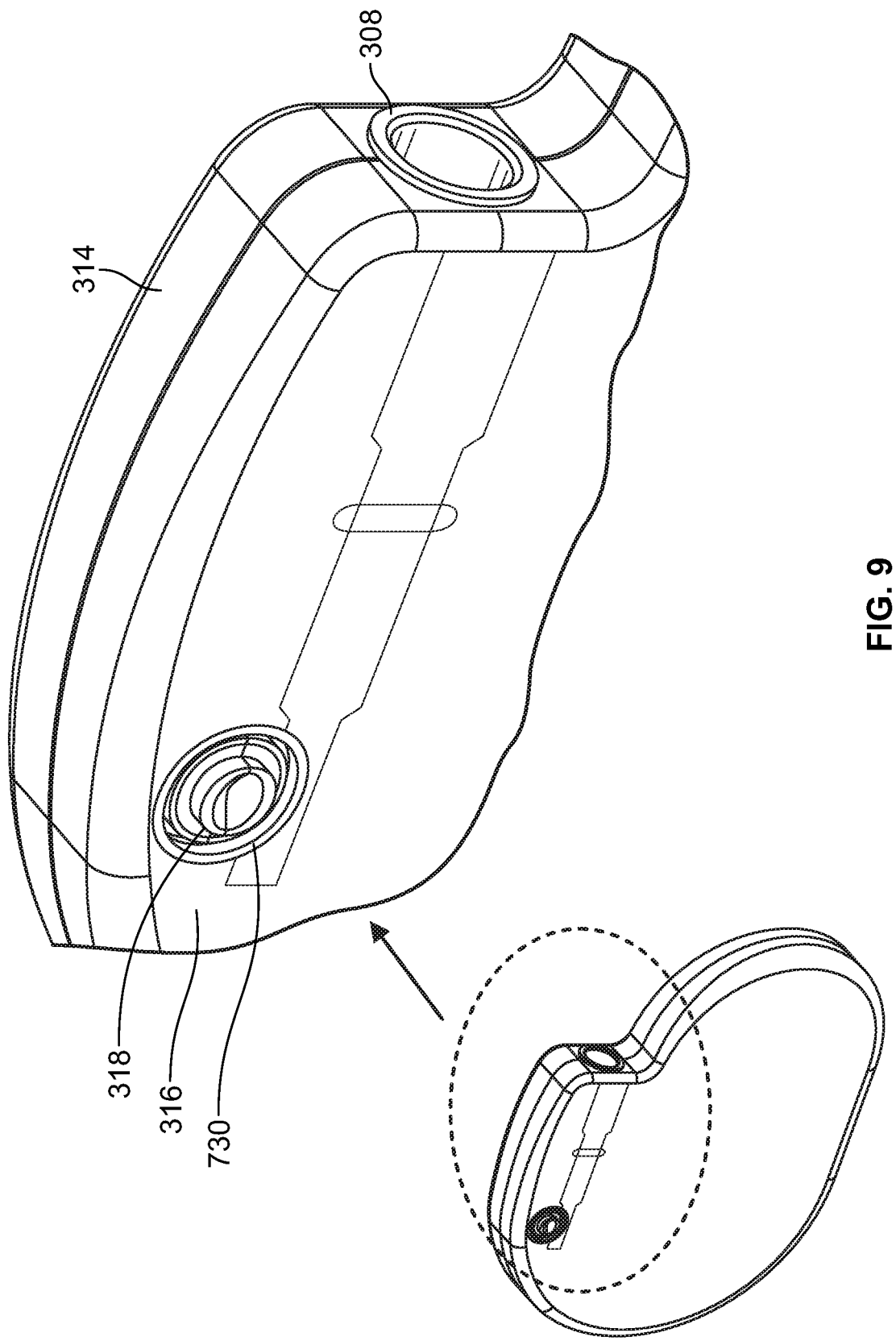
FIG. 9 illustrates a partial side perspective view of the IMD of FIG. 1 in accordance with embodiments herein.

FIG. 9 illustrates a partial side perspective view of the IMD of FIG. 1 in accordance with embodiments herein. The septum opening 730 may be hermetically joined to the case body. For example, the septum opening 730 may include a metallic ring that is joined to the case body by welding, brazing or the like. The septum 318 may be sealed within the septum connector 730. Additionally or alternatively, the connector opening 308 may be hermetically joined to the case body. For example, the connector opening 308 may also be joined to the case body by welding, brazing or the like. The connector opening 308 may include a chamfer disposed circumferentially around an inner circumferential edge thereof configured to provide strain relief to a lead and/or a lead connector assembly 312 engaged in the receptacle assembly 508.

Figure 10:
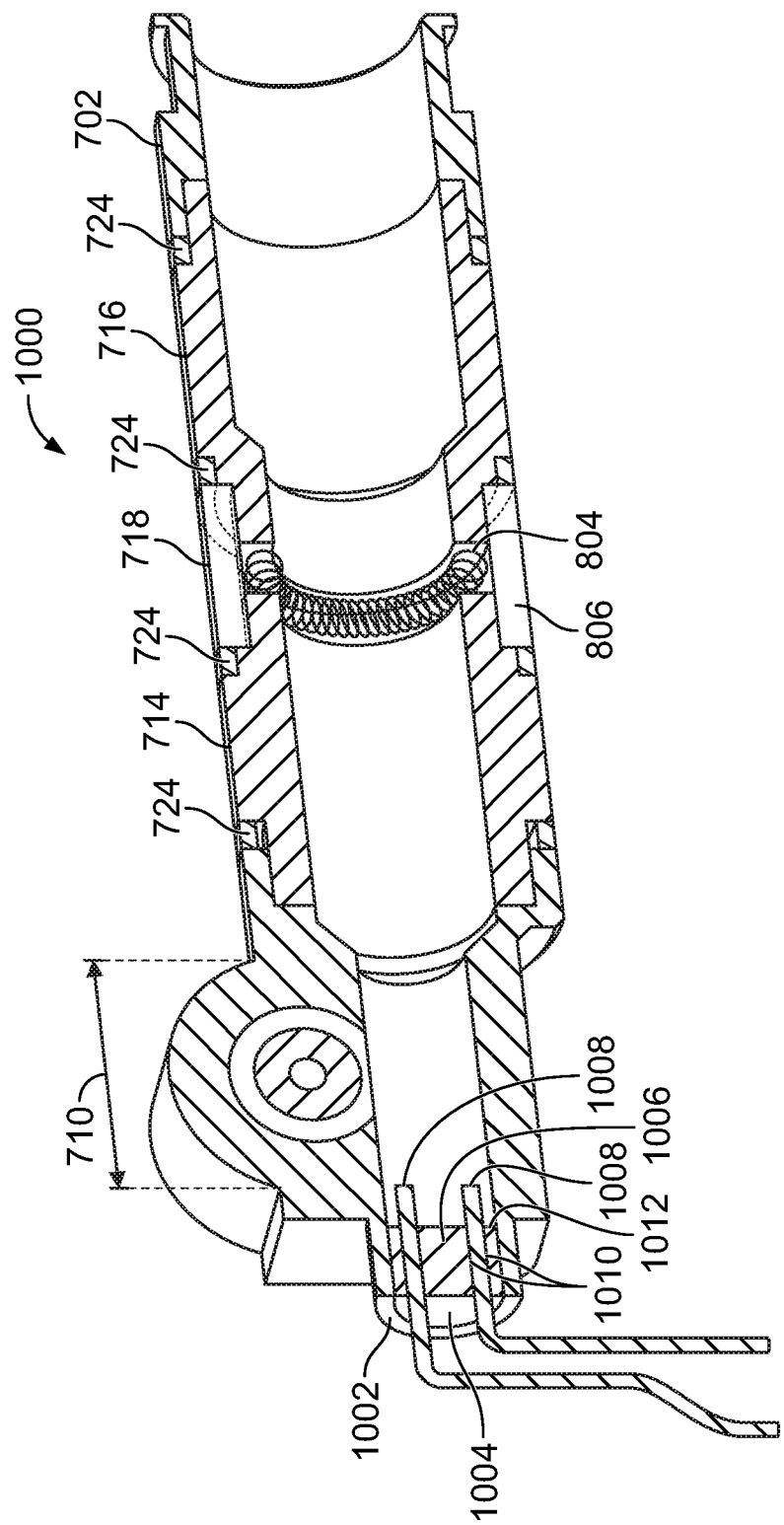
FIG. 10 illustrates a sectional view of another receptacle assembly in accordance with embodiments herein.

FIG. 10 illustrates a sectional view of another receptacle assembly in accordance with embodiments herein. The receptacle assembly 1000 may be similar in all aspects to the receptacle assembly 508 except as otherwise described. A proximal tip 1002 of the receptacle assembly includes a hermetic pin assembly 1004 disposed therein. The hermetic pin assembly 1004 may include a ceramic block 1006 hermetically joined to pins 1008 extending therethrough via sputtered intermediate members 1010. The hermetic pin assembly 1004 may be hermetically joined to the tip 1002 via another sputtered intermediate member 1012 disposed on and extending circumferentially around an external surface of the ceramic block 1006. The pins 1008 of the hermetic pin assembly 1004 may electrically couple portions of the lead engagement assembly 710 to IMD circuitry provided in the electronics module 504.

Figure 11:
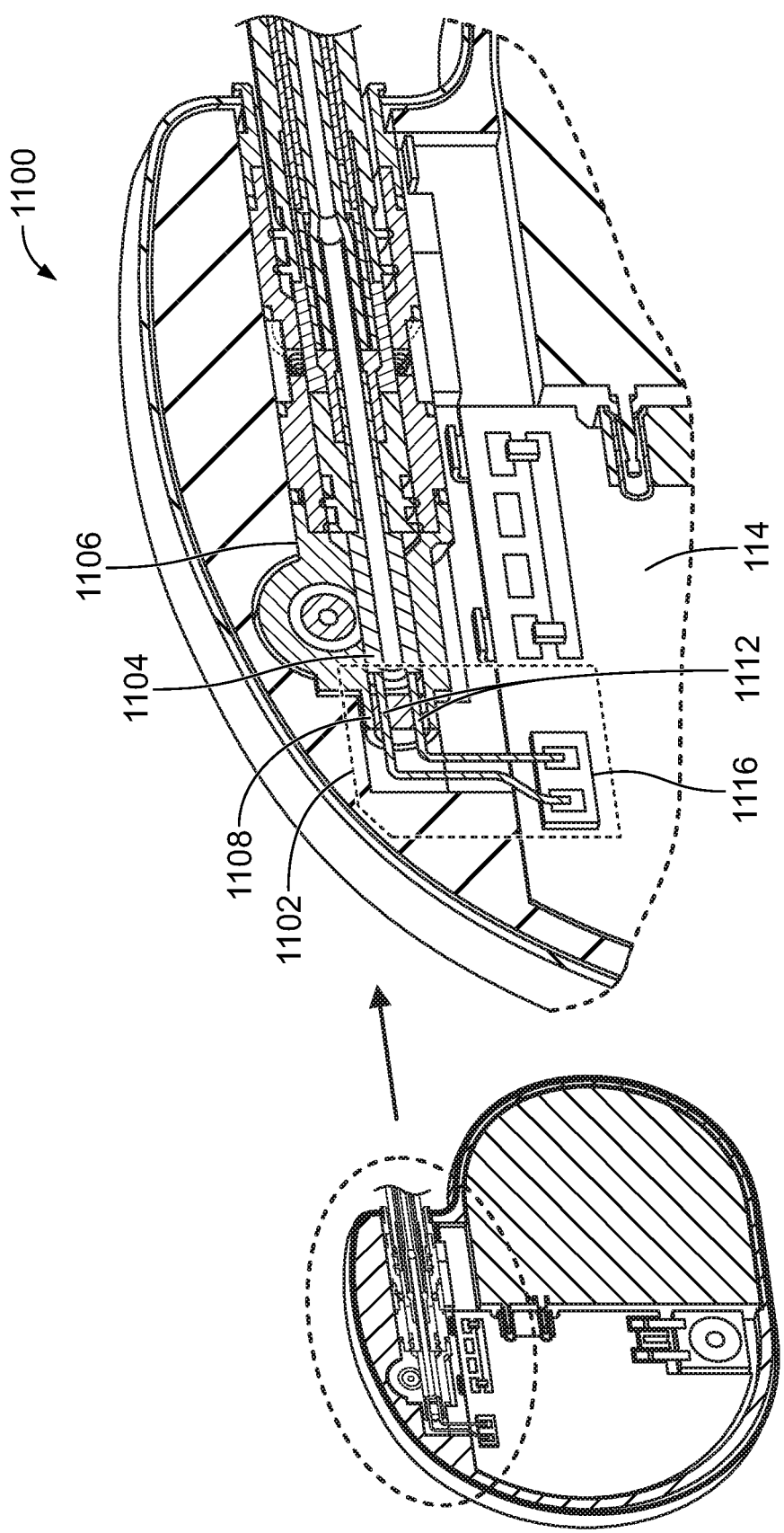
FIG. 11 illustrates a sectional view of an example implementation of a lead engagement sensing circuit in accordance with embodiments herein.

FIG. 11 illustrates a sectional view of an example implementation of a lead engagement sensing circuit in an IMD in accordance with embodiments herein. The IMD 1100 may be formed generally in the same manner as described with respect to one or more of FIGS. 1-10 or may be a conventional IMD having a separate header formed on or joined to an IMD housing. The IMD 1100 includes a lead engagement sensing circuit 1102 that may be configured to detect when a lead connector assembly 1104 is engaged with a receptacle assembly 1106. Based on the lead connector assembly 1104 being engaged within the receptacle assembly 1106, the proximal end of the lead connector assembly 1104 contacts the lead engagement sensing circuit 1102. The proximal end of the lead connector assembly 1104 may contact the first end of pins 1112 disposed at and extending through a proximal tip 1108 of the receptacle assembly 1106. In one example implementation, the proximal tip 1108 includes a hermetic pin assembly 1110 disposed therein that is similar to the hermetic pin assembly 1104 of FIG. 10. The second end of the pins 1112 may be electrically coupled to one or more of the IMD circuitry disposed in the electronics module 1114 and/or a feedback circuit 1116. The feedback circuit 1116 may provide a signal to indicate that the lead is properly engaged within the receptacle assembly 1106. The signal may be perceptible by a clinician during implantation of the IMD 1100. Additionally or alternatively, the signal may be inductively or telemetrically transmitted to an external electronics device 104 to confirm proper lead engagement. One or more processors associated with the IMD, such as the microcontroller 164, may only implement a lead engagement detection algorithm during a set-up procedure associated with the IMD 100. Accordingly, the lead detection circuit 1102 provides an objective means for verifying proper lead engagement in a receptacle assembly integrated within a common chamber of the case body of an IMD in accordance with one or more of FIGS. 1-10 or within a conventional header formed on or joined to an IMD housing.

Methods for Forming a Header-Less IMD

Figure 12:
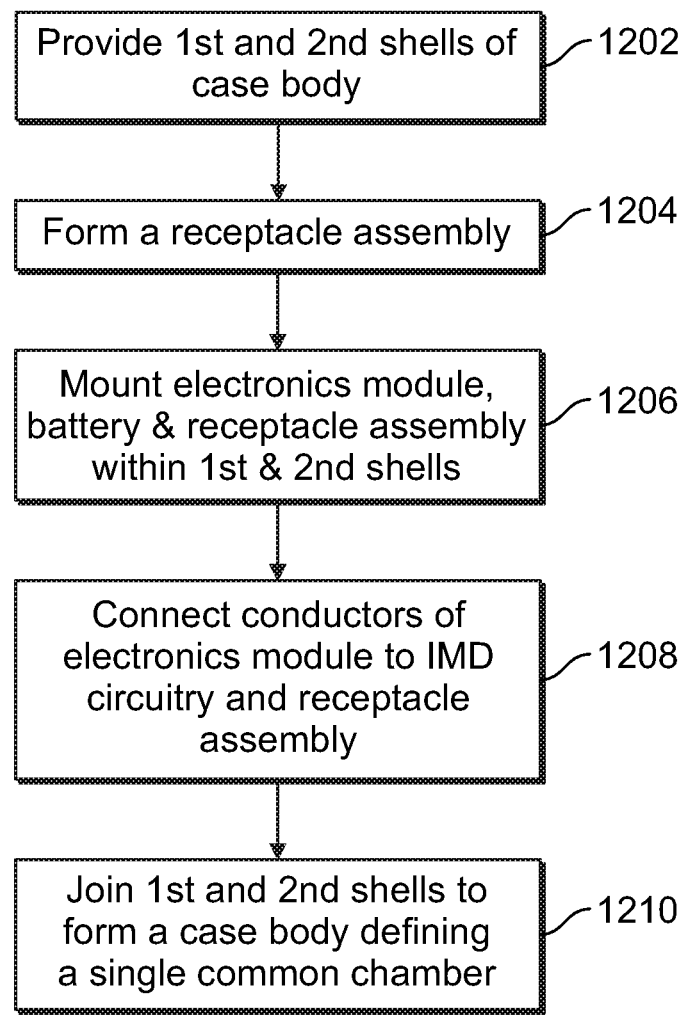
FIG. 12 illustrates a process for forming a header-less IMD in accordance with embodiments herein.

FIG. 12 illustrates a process for forming a header-less IMD carried out in accordance with embodiments herein, such as in accordance with one or more of FIGS. 1-11. Although the operations of FIG. 12 are described in at least a partially serial manner, it is recognized that at least a portion of the operations may be performed in parallel.

At 1202, first and second shells 314, 316 of a case body of a device housing 101 are provided or obtained. The case body including a connector opening 308 provided in one or more of the first and second shells 314, 316.

At 1204, a receptacle assembly 508 is formed. The receptacle assembly 508 includes an interior chamber 706 and a receptable inlet 702 configured to receive a lead connector assembly 312. The receptacle assembly 508 may be formed by sandwiching a contact element 718 between first and second non-conductive support elements 714, 716. The contact element 718 and the first and second non-conductive support elements 714, 716 may wrap about the interior chamber 706. The contact element 718 may be bonded to the first and second non-conductive support elements 714, 716 to form a hermetic seal therebetween. For example, the first and second non-conductive support elements 714, 716 may be formed from a ceramic material. A conductive intermediate material 724 (e.g., gold) may be sputtered onto portions of the first and second non-conductive support elements 714, 716. The contact element 718 may be joined by brazing or the like to the first and second non-conductive elements 714, 716 via the intermediate material 724. The hermetic seal formed thereby may separate the interior chamber 706 from the single common chamber 502 within the case body.

Additionally or alternatively, forming the receptacle assembly 508 may include forming the contact element 718. Forming the contact element 718 may include arranging a contact ring 806 concentric with a contact spring 804. The contact spring 804 may extend about and protrude into the interior chamber 706 and the contact ring 806 may extend circumferentially about the contact spring 804 to provide a direct electrical connection to the hermetic interior chamber 706 of the receptacle assembly 508.

At 1206, an electronics module 504 including circuitry, a battery 506, and the receptacle assembly 508 are mounted within the first and second shells 314, 316. The electronics module 504 may include a flexible circuit having conductors with first and second ends. Mounting the receptacle assembly 508 may include locating the receptacle inlet 702 at the connector opening 308.

At 1208, a first end of the conductors is connected to the circuitry of the IMD 100 and the second end of the conductors is connected to the receptacle assembly in a feedthrough-less configuration. For example, the second end of the conductors may be electrically connected to the contact ring 806 of the contact element 718 to directly electrically couple the interior chamber 706 of the receptacle assembly 508 to the circuitry of the electronics module 504.

At 1210, the first and second shells 314, 316 are joined to form the case body. The joining may include hermetically sealing the first and second shells 314, 316 with one another. The case body may include side walls 302, 304 and a peripheral edge 306 that define a single common chamber 502. The electronics module 504, the battery 506, and the receptacle assembly 508 are provided within the single common chamber 502. The joining may include joining the receptacle inlet 702 to the connector opening 308 to form a passage through the case body into the interior chamber 706 of the receptacle assembly 508. The receptacle assembly 508 may be held within the single common chamber 502 of the case body in a header-less configuration.

Accordingly, the present systems, devices, and methods provide for header-less IMDs. Such systems, devices, and methods provide for integration of a receptacle assembly into a single common chamber of the case body of the IMD in a header-less configuration. Additionally or alternatively, the systems, devices, and methods provide for a receptacle assembly having an interior chamber that is hermetically sealed from the single common chamber housing the electronics module, the battery, and the receptacle assembly. A feedthrough-less, non-hermetic connection between the hermetic interior chamber of the receptacle assembly and the IMD circuitry may also be provided. Further additionally or alternatively, the present systems, devices, and methods provide for a lead engagement detection circuit that is configured to detect when the lead connector assembly is engaged within the receptacle assembly.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. A header-less implantable medical device, comprising:
an electronics module including circuitry;
a battery;
a receptacle assembly having an interior chamber and a receptacle inlet configured to receive a lead connector assembly;
a device housing having a case body that includes side walls and a peripheral edge that define a single common chamber, the electronics module and the battery provided within the single common chamber, the receptacle assembly also provided within the single common chamber and directly connected to the electronics module in a feedthrough-less configuration; and
a connector opening provided in the case body and joined to the receptacle inlet to form a passage through the case body into the interior chamber of the receptacle assembly.

2. The device of claim 1, wherein the receptacle assembly includes a contact element extending at least partially about the interior chamber and configured to directly engage a terminal at a proximal end of the lead connector assembly, wherein the electronics module further comprises a flexible circuit having conductors with first and second ends, the first end connected to the circuitry and the second end directly connected to the contact element in the feedthrough-less configuration.

3. The device of claim 1, wherein the case body has generally planar opposed side walls and the peripheral edge that has an envelope that is generally oval shaped, the peripheral edge has a notch formed therein to provide a flat surface at the connector opening.

4. The device of claim 1, wherein the case body includes first and second shells that are hermetically sealed with one another to form the single common chamber.

5. The device of claim 4, wherein the first and second shells include upper and lower sections, the upper section enclosing the receptacle assembly, the lower section enclosing the electronics module and the battery, the upper and lower sections of each of the first and second shells formed from monolithic homogeneous material.

6. The device of claim 1, wherein the interior chamber includes sealing flanges wrapping about an interior of the interior chamber, the sealing flanges formed of a non-conductive material, the sealing flanges configured to flex and frictionally receive the lead connector assembly to prevent bodily fluid from migrating along the lead connector assembly into the interior chamber.

7. The device of claim 1, wherein the receptacle assembly includes a contact element sandwiched between first and second non-conductive support elements, the contact element configured to directly engage a terminal at a proximal end of the lead connector assembly, the contact element and the first and second non-conductive support elements wrapping about the interior chamber, the contact element bonded to the first and second non-conductive support elements to form a hermetic seal separating the interior chamber from the single common chamber within the case body.

8. The device of claim 7, wherein the contact element includes a contact spring and a contact ring arranged concentric with one another, the contact spring extending about and protruding into the interior chamber, the contact ring extending circumferentially about the contact spring and electrically connected to the electronics module.

9. The device of claim 7, further comprising a lead engagement sensing circuit configured to detect when the lead connector assembly is engaged with the receptacle assembly.

10. The device of claim 1, further comprising a lead having a proximal end that includes the lead connector assembly and a distal end with one or more electrodes, the lead configured to at least one of: i) sense activity or ii) deliver a stimulus to tissue surrounding the one or more electrodes.

11. An implantable system, comprising:
an electronics module including circuitry;

a battery;

a receptacle assembly having an interior chamber and a receptacle inlet configured to receive a lead connector assembly;

a device housing having a case body that includes side walls and a peripheral edge that define a single common chamber, the electronics module and the battery provided within the single common chamber, the receptacle assembly also provided within the single common chamber and directly connected to the electronics module in a feedthrough-less configuration;

a connector opening provided in the case body and joined to the receptacle inlet to form a passage through the case body into the interior chamber of the receptacle assembly; and a lead having a proximal end that includes the lead connector assembly and a distal end with one or more electrodes, the lead configured to at least one of: i) sense activity or ii) deliver a stimulus to tissue surrounding the one or more electrodes.

12. The system of claim 11, wherein the receptacle assembly includes a lead engagement assembly, the lead engagement assembly including a set screw advanceable within a threaded bore configured to retain the proximal end of the lead connector assembly.

13. The system of claim 12, wherein one or more of the case body or the lead engagement assembly includes an integrated septum, the septum configured to allow access to a head of the set screw while inhibiting ingress of fluids into the lead engagement assembly.

14. The system of claim 11, wherein the interior chamber includes sealing flanges wrapping about an interior of the interior chamber, the sealing flanges formed of a non-conductive material, the sealing flanges configured to flex and frictionally receive the lead connector assembly to prevent bodily fluid from migrating along the lead connector assembly into the interior chamber.

15. The system of claim 11, wherein the receptacle assembly includes a contact element sandwiched between first and second non-conductive support elements, the contact element configured to directly engage a terminal at the proximal end of the lead connector assembly, the contact element and the first and second non-conductive support elements wrapping about the interior chamber, the contact element bonded to the first and second non-conductive support elements to form a hermetic seal separating the interior chamber from the single common chamber within the case body.

16. A method to provide header-less implantable medical device, comprising:

providing first and second shells of a case body of a device housing, the case body including a connector opening provided in one or more of the first and second shells;

mounting an electronics module including circuitry, a battery, and a receptacle assembly within the first and second shells, the receptacle assembly having an interior chamber and a receptacle inlet configured to receive a lead connector assembly, the mounting including locating the receptacle inlet at the connector opening; and joining the first and second shells to form the case body, the case body including side walls and a peripheral edge that define a single common chamber, the circuitry and the battery provided within the single common chamber, the receptacle assembly also provided within the single common chamber and directly connected to the electronics module in a feedthrough-less configuration, the joining including joining the receptacle inlet to the connector opening to form a passage through the case body into the interior chamber of the receptacle assembly.

17. The method of claim 16, wherein the receptacle assembly is held within the single common chamber of the case body in a header-less configuration.

18. The method of claim 16, wherein the electronics module further comprises a flexible circuit having conductors with first and second ends, the method further comprising connecting a first end of the conductors to the circuitry and connecting the second end to the receptacle assembly in the feedthrough-less configuration.

19. The method of claim 16, wherein the joining includes hermetically sealing the first and second shells with one another.

20. The method of claim 16, further comprising forming the receptacle assembly, forming the receptacle assembly including sandwiching a contact element between first and second non-conductive support elements and bonding the contact element to the first and second non-conductive support elements to form a hermetic seal therebetween, each of the contact element and the first and second non-conductive support elements wrapping about the interior chamber, and the hermetic seal separating the interior chamber from the single common chamber within the case body.

21. The method of claim 20, further comprising forming the contact element, forming the contact element including arranging a contact ring concentric with a contact spring such that the contact spring extends about and protrudes into the interior chamber and the contact ring extends circumferentially about the contact spring to provide a direct electrical connection to the interior chamber for the circuitry of the electronics module.

* * * * *